US010898130B2

(12) United States Patent
John et al.

(10) Patent No.: US 10,898,130 B2
(45) Date of Patent: *Jan. 26, 2021

(54) SYSTEM AND METHOD FOR PAIN DETECTION AND COMPUTATION OF A PAIN QUANTIFICATION INDEX (71) Applicant: New York University, New York, NY (US)

(72) Inventors: Erwin Roy John, Mamaroneck, NY (US); Leslie S. Prichep, Mamaroneck, NY (US); Emile Hiesiger, New York, NY (US)

(73) Assignee: New York University, New York, NY (US)

( * ) Notice: Subject to any disclaimer, the term of this patent is extended or adjusted under 35 U.S.C. 154(b) by 905 days.

This patent is subject to a terminal disclaimer.

(21) Appl. No.: 15/195,716

(22) Filed: Jun. 28, 2016

(65) Prior Publication Data
US 2016/0302720 A1 Oct. 20, 2016

Related U.S. Application Data (63) Continuation of application No. 11/697,217, filed on Apr. 5, 2007, now Pat. No. 9,402,558.

(51) Int. Cl.
A61B 5/0476 (2006.01)
A61B 5/00 (2006.01)
A61B 5/0482 (2006.01)

(52) U.S. Cl.
CPC .......... A61B 5/4824 (2013.01); A61B 5/0476 (2013.01); A61B 5/0482 (2013.01);
(Continued)

(58) Field of Classification Search
CPC ..... A61B 5/0476; A61B 5/0478; A61B 5/048; A61B 5/0482; A61B 5/0484;
(Continued)

(56) References Cited

U.S. PATENT DOCUMENTS 5,083,571 A    1/1992  Prichep
6,018,675 A *  1/2000  Apkarian ............. A61B 5/4824
                                                          600/407
(Continued)

OTHER PUBLICATIONS

Specht, Donald F. "Probabilistic Neural Networks." Neural Networks, vol. 3. pp. 109 118, 1990. (Year: 1990).*
(Continued)

Primary Examiner — Meredith Weare
(74) Attorney, Agent, or Firm — Fay Kaplun & Marcin, LLP (57) ABSTRACT A method of detecting pain in a subject, comprises the steps of generating brain wave data based on brain wave activity of the subject and comparing the brain wave data to reference data to generate result data, the reference data corresponding to at least one of (i) population normative data indicative of brain wave activity of a first plurality of individuals in an absence of pain, (ii) population reference data indicative of brain wave activity of a second plurality of individuals generated in response to pain events inflicted on the second plurality of individuals, (iii) subjective population reference data indicative of brain wave activity of a third plurality of individuals reporting a sensation of pain, and (iv) population of reference data indicative of brain wave activity of a fourth population of individuals following an intervention which has changed a subjective report of pain in combination with determining a presence of pain experienced by the subject as a function of the result data.

21 Claims, 5 Drawing Sheets (52) U.S. Cl.
CPC ............ *A61B 5/483* (2013.01); *A61B 5/7264* (2013.01); *A61B 2503/40* (2013.01); *A61B 2560/0223* (2013.01)

(58) Field of Classification Search
CPC ............ A61B 5/04842; A61B 5/04845; A61B 5/04847; A61B 5/4821; A61B 5/4824; A61B 5/4827; A61B 5/483
See application file for complete search history.

(56) References Cited

U.S. PATENT DOCUMENTS

| | | | | |
|---|---|---|---|---|
| 6,317,627 | B1* | 11/2001 | Ennen | A61B 5/0476 600/300 |
| 6,907,280 | B2 | 6/2005 | Becerra et al. | |
| 6,950,698 | B2* | 9/2005 | Sarkela | A61B 5/0478 600/544 |
| 9,402,558 | B2* | 8/2016 | John | A61B 5/0476 |
| 2002/0042563 | A1* | 4/2002 | Becerra | A61B 5/055 600/407 |
| 2003/0144601 | A1* | 7/2003 | Prichep | A61B 5/0476 600/544 |
| 2004/0079372 | A1 | 4/2004 | John et al. | |
| 2006/0089551 | A1* | 4/2006 | England | A61B 5/055 600/411 |
| 2006/0120584 | A1* | 6/2006 | Hillman | G06F 19/321 382/128 |
| 2006/0241562 | A1 | 10/2006 | John et al. | |
| 2007/0100251 | A1* | 5/2007 | Prichep | A61B 5/04009 600/544 |

OTHER PUBLICATIONS

Richeimer, Steven. "The Assessment of the Patient with Pain." 2000. (Year: 2000).*

Mueller et al. "Treatment of Fibromyalgia Incorporating EEG-Driven Stimulatioin: A Clinical Outcomes Study." 2001. Journal of Clinical Psychology. vol. 57(7), 933-952. (Year: 2001).*

* cited by examiner

SYSTEM AND METHOD FOR PAIN DETECTION AND COMPUTATION OF A PAIN QUANTIFICATION INDEX

PRIORITY CLAIM

The present application is a Continuation of U.S. patent application Ser. No. 11/697,217 filed Apr. 5, 2007, now U.S. Pat. No. 9,402,558. The disclosure of the above patent(s)/application(s) is incorporated herein by reference.

BACKGROUND

Pain measurement has generally been substantially subjective. That is, while diagnostic procedures (e.g., MRI, x-ray, ultrasound, etc.) provide data allowing for accurate determinations of the physiological condition, pain is almost always measured by asking for feedback from the patient. For example, in situations where opioids and/or other analgesics are being administered, and particularly, in Patient Controlled Analgesia (PCA), it would be desirable to measure objectively the pain experienced by the patient to surveil, and possibly over-ride, unwarranted and excessive administration of analgesia. Undertreatment of acute and especially chronic pain is widespread and often occurs because physicians have no objective way to assess patients' pain reports, especially in cases where the source of pain is not identifiable on routine anatomically based radiological studies or routine diagnostic electrophysiological studies of the peripheral nervous system. Even in emergency departments, when evaluating or treating a patient with a broken leg or dislocated shoulder, the staff may undertreat or overtreat with analgesia, selecting the level based on little more than past experience on the assumption that all patients respond similarly to similar doseages.

The lack of such objective assessment also impairs the control of Patient Controlled Analgesia (PCA)—narcotics delivered intravenously via a pump controlling both a basal rate of the dose infused hourly as well as a dose and frequency of additional narcotic a patient may self administer per hour. If a patient is in pain despite the basal and additional bolus narcotic administration, the pump parameters must be adjusted upward. This process which requires the attention of trained nursing staff and the orders of a physician may cause unfortunate delay and unnecessary pain before the PCA parameters are properly adjusted. Furthermore, relying heavily on patient reports of pain provides opportunities for patients to manipulate the physician to obtain more pain medication than is necessary.

As animals are unable to provide subjective assessments of their pain levels and the extent of discomfort can only be guessed at by noting behavioral changes (e.g., limping), an objective measurement of pain would be particularly valuable.

In addition to medical applications, quantitative reference data may be important in any situation where it may be necessary to objectively assess a level of pain (e.g., lawsuits, insurance and disability claims, etc.).

Brain imaging methods such as Positron Emission Tomography (PET), Single Photon Emission Computed Tomography (SPECT) and Functional Magnetic Resonance Imaging (fMRI) are sometimes used to help understand pain processing mechanisms in those with acute, experimentally created, and less commonly, chronic pain. Low resolution qEEG brain imaging methods such as LORETA (Pascual-Marqui et al 1999) may be used to provide physiological information about the brain regions involved in processing various types of acute and/or chronic pain, as well as the effect of treatment on the physiological activity of these regions but have provided no objective measures of pain.

SUMMARY OF THE INVENTION

The present invention is directed to a system and method for detecting pain. The method comprises the steps of generating brain wave data based on brain wave activity of a subject, comparing the brain wave data to reference data to generate result data, and determining a presence of pain experienced by the subject as a function of the result data. The reference data corresponds to at least one of (i) population normative data indicative of brain wave activity of a first plurality of individuals in an absence of pain, (ii) population reference data indicative of brain wave activity of a second plurality of individuals generated in response to a pain event inflicted on the individuals, (iii) self normative data indicative of brain wave activity of the subject in an absence of pain and (iv) subjective population reference data indicative of brain wave activity of a third plurality of individuals reporting a sensation of pain. As would be understood by those skilled in the art, the various pluralities of individuals from whom data is obtained may be entirely separate from one another or may overlap partially or entirely. In addition, those skilled in the art will understand that any data based on reports of pain by individuals or patients may be either in response to prompts for this information or spontaneously offered.

DETAILED DESCRIPTION

The present invention may further understood with reference to the following description and the appended drawings, wherein like elements are provided with the same reference numerals. The present invention describes a system and method for detecting pain by analyzing brain wave data collected from an electroencephalogram (EEG). Those skilled in the art will understand that other types of data relating to brain activity may be manipulated in a manner similar to that described herein to achieve similar results. Thus, the description of EEG and the specific descriptions of EEG features are illustrative of exemplary embodiments of the invention and should not be construed to limit the scope of this invention. For example, activity of any body system sensitive to pain (e.g., autonomic nervous system, sweating or galvanic skin response (GSR), tearing of the eyes, contraction of muscles on the forehead—frontalis, orbicularis, skin around the eyes, etc.) may be measured and quantified to determine whether a subject is experiencing pain. Additionally, other analysis modalities which are sensitive to the amount of neuronal and/or metabolic activity in any brain region(s) may be utilized, e.g., electromyogram (EMG), magneto-encephalogram (MEG), functional magnetic resonance imaging (fMRI), near infrared spectroscopy (NIRS) or other optical tomographic methods (e.g., SPECT), etc.

Although the invention is described in detail with regard to human subjects, those skilled in the art will understand that substantially similar methods may be used to obtain the same results for animals, Specifically, after making adjustments for anatomical differences mammals such as horses, cats, dogs, etc. may be subjected to analyses similar to that described for humans. Initially, this animal analysis may more commonly apply self norms by comparing brain activity for an individual before and after the onset of pain (e.g., before and after a surgical procedure) than by comparing brain activity of a subject to population data. However, those skilled in the art will understand that population data for animals may be compiled in the same manner described below for human subjects.

As would be understood by those skilled in the art, an electroencephalogram (EEG) detects neurophysiological activity by measuring an intensity and pattern of electrical signals generated by the brain. Spontaneous oscillations in the electrical signals are typically referred to as brain waves or EEG. The EEG is a record derived from the spontaneously oscillating electrical signals and other electrical activity (e.g., "noise" or electrical activity of a non-cerebral origin, transient potentials elicited by sensory stimuli, e.g., event-related potentials (ERPs), etc.). The EEG is typically used to assist in the diagnosis, in children and adults, of epilepsy, space occupying lesions, neurological and psychiatric disorders and other abnormalities of brain function.

In the exemplary embodiment, data corresponding to brain activity (e.g., EEG data) is utilized to detect and quantify pain experienced by a subject. Differences between brain waves produced in the presence and absence of pain, as well as differences indicative of varying levels of pain, are assessed statistically by a comparison of the subject's EEG data to data in one or more databases. For example, the subject's EEG data may be compared to normative data indicative of normal brain wave activity for a control population comprised of individuals substantially similar to the subject (e.g., age, gender, etc.). The subject's EEG data may further be compared to caled or "calibrated" reference data indicative of brain wave activity of the control population in the presence of varying of degrees of pain introduced, for example, by incremental quantified stimulation. The database may further include self-normative data indicative of the subject's brain wave activity in the presence and absence of pain, and/or self-reported reference data collected from the control population indicating brain wave activity when individuals within the population subjectively report the presence of pain (e.g., acute, chronic). The database may further include medical histories and physical and/or neurological examination results for individuals in the population and/or the subject. Those skilled in the art will understand that the term database is not being used to connote a specific data structure. Rather, it is to be understood broadly to include any searchable collection of data records residing in any type of memory.

The present invention relates to a system and method for detecting, quantifying and imaging pain, the Pain Quantification Index/Image. The method comprises the steps of extracting quantitative electroencephalographic (qEEG) features from brain electrical activity recorded from varying numbers of electrodes located at standardized positions on the scalp and forehead of a subject, comparing the brain wave data to age-appropriate normative data to generate standard or Z-score result data, and determining the presence and/or chronicity and/or intensity of pain experienced by the subject as a function of the result data. The database corresponds to at least one of (i) population normative data indicative of brain wave activity of a first plurality of individuals in an absence of pain, (ii) population reference data indicative of brain wave activity of a second plurality of normal individuals generated in response to a series of calibrated pain events inflicted on the individuals, (iii) subjective population reference data (chronic and acute) indicative of brain wave activity of a third plurality of individuals reporting a graded or scaled sensation of pain; and (iv) population of reference data (chronic and acute cases) reflective of brain wave activity of a fourth plurality of individuals following an intervention which has changed the state of their subjective report of pain.

The result data can be used for source localization of the most probable neuroanatomical generators within the brain of the abnormal qEEG activity that was detected on the scalp by the PDI. Low Resolution Electromagnetic Tomographic Analysis (Pascual-Marqui et al 1999), Variable Resolution Electromagnetic Tomographic Analysis (Bosch-Bayard et al 2001) or similar methods are exemplary of the inverse solution techniques that may be used to visualize these sources. The computed sources may be depicted upon transaxial, sagittal or coronal slices from the Probabilistic MRI Atlas (Evans et al 1993), color coding each voxel in each brain region using a palette to represent ther statistical significance of the detected source(s). These LORETA images can be computed by an instrument that uses an appropriate array of electrodes placed upon the scalp, in accordance with the International 10/20 Electrode Placement System (Jasper 1958) and implements all computations from a set of digital amplifiers controlled and analyzed by a personal desktop or laptop computer.

Figure 1:
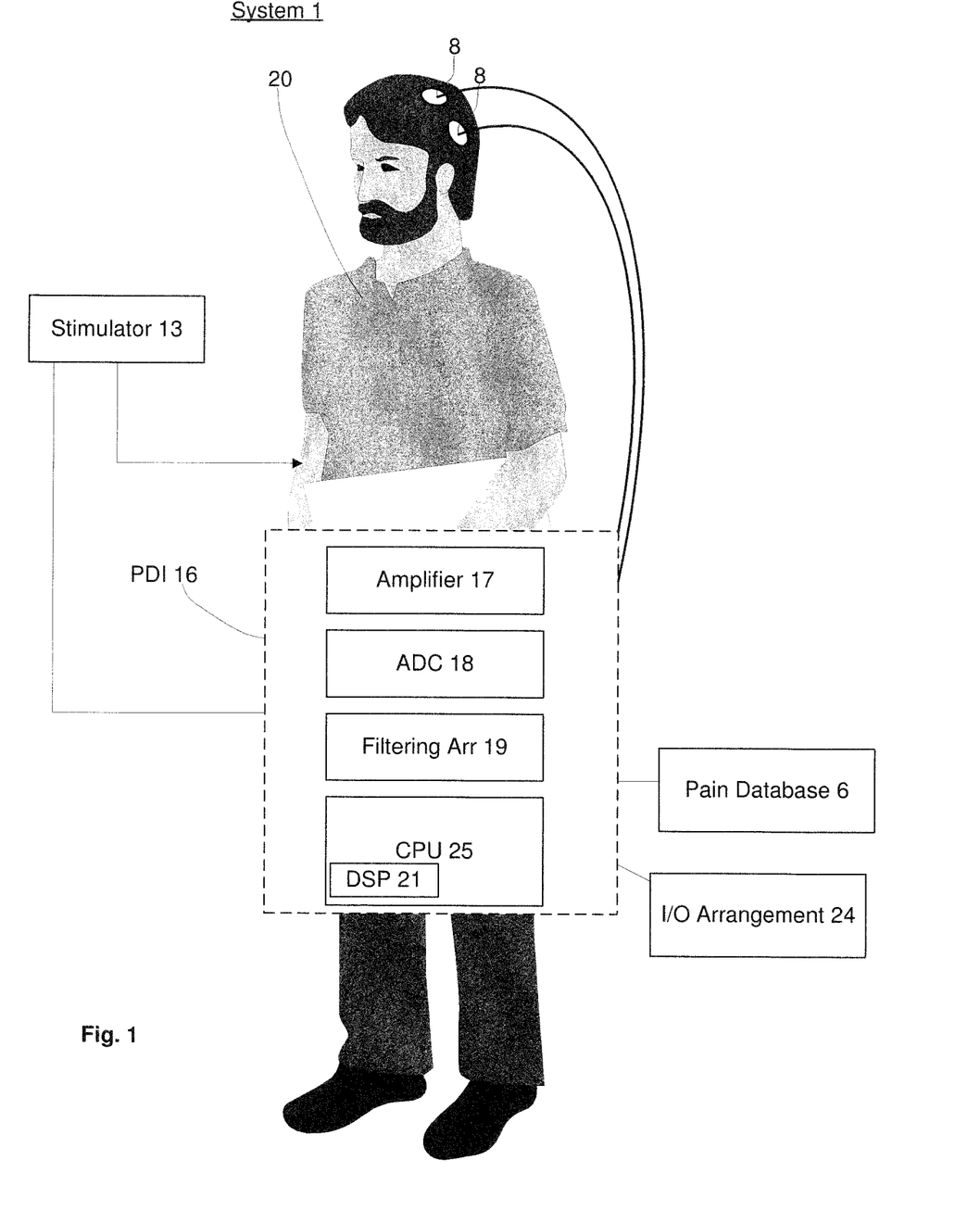
FIG. 1 shows an exemplary embodiment of a system for detecting pain according to the present invention.

FIG. 1 shows an exemplary embodiment of a system 1 for pain detection according to the present invention. The system 1 includes a pain detecting instrument (PDI) 16 which provides objective corroboration, and optionally quantification, of the pain experienced by a subject 20 at a given time. In the exemplary embodiment, the PDI 16 is implemented as a portable, handheld device for use in clinical and non-clinical settings. In an example of the latter case, an EMT or other medical personnel in the field may use the PDI 16 to detect and/or quantify pain experienced by a subject to, for example, determine an appropriate pain management strategy or, in conjunction with palpation, etc. assist in making a preliminary diagnosis. The pain quantified by, for example, a comparison of the subject's EEG data to a pain quantification index may be recorded for future reference in patient records, employer records of work-related injuries, etc. Those of skill in the art will understand that the PDI 16 may be utilized in various other situations including, but not limited to, management of acute and/or chronic pain, rehabilitation treatment, treatment prescription, evaluation of treatment efficacy, monitoring or regulating delivery of analgesic to patients, including patient controlled analgesic (PCA) delivery, differentiating between levels of pain, reducing pain through appropriate neurofeedback paradigms, etc.

The PDI 16 is coupled to electrode(s) 8 to receive electrical data corresponding to brain activity of the subject 20. Similar electrode placements may be used to record the SEP or EEG. Electrode(s) may be placed in a standard array such as the International 10/20 Electrode Placement System (Jasper 1958) or in selected advantageous positions on the head, forehead or cheeks. The electrical data is quantitatively analyzed to generate digital quantitative EEG (qEEG) data and/or quantitative somatosensory evoked potential (qSEP) data which is then compared with reference data in a database 6. As would be understood by those skilled in the art, the database 6 may be stored in a memory within the PDI 16 or may be accessed from a remote storage via, for example a wireless or wired connection. Alternatively, portions of the database 6 may be stored locally while others are accessed from one or more remote locations. As will be described in more detail below, the reference data in the database 6 corresponds to brain wave data detected from: (i) individuals experiencing various levels of pain from no pain to extreme levels of pain (calibrated pain norms), as determined experimentally and explained further below; (ii) individuals with acute or chronic pain (the subject 20) seen in the absence of pain (self-referenced norm); and/or (iii) individuals self-reporting pain (acute or chronic). A comparison of the subject's brain wave data with the database 6 indicates a presence/absence of pain and a quantification of any pain experienced. Changes in the EEG data and/or the SEP data may correlate to conditions in the database 6. In a pain treatment protocol/procedure, for example, comparing the subject's brain wave data before and after the treatment to the reference data may be used to quantify neurobiological effectiveness of the treatment or procedure and/or guide further treatment.

In constructing the database 6, an EEG and/or SEP may be generated for each individual in the population, and the EEG and the SEP are analyzed to generate the reference data. For example, a resting EEG and/or SEP may be analyzed to extract features correlated with subjective reports of pain (and corresponding intensity and/or chronicity) by the individuals. As understood by those of skill in the art, peaks in an EEG power spectra reflect spontaneous activation of different neuronal ensembles in the brain regions sampled by the electrodes 8. The successive peaks in the waveshapes of SEPs correspond to processing of signals related to stimuli administered to the subject 20 as the signals pass through sequential anatomical regions, e.g., the medial lemniscal pathway structures of the nervous system. The shape of the EEG power spectrum and/or timing of peaks in the SEP (e.g., latency periods) provide information regarding functioning of the nervous system and processing of the signals through neuronal transmission pathways.

In particular, distinctive changes in power may occur at particular frequencies in the EEG power spectrum when recorded from particular portions of the scalp, e.g., in a preferred exemplary embodiment, from a dorsolateral, prefrontal lead, a periorbital prefrontal lead, a mesial frontal lead over the anterior cingulate gyrus, a midline or lateralized lead in central, parietal or other regions over a cortical areas sensitive to spontaneous activity arising from acute or chronic painful sensory inputs reaching cortical regions which correspond to the sensation of pain. Such distinctive reactions to pain are extracted from the database(s) 6 and are used to define a "qEEG pain signature" which constitutes a critical set of features for a "qEEG pain discriminant function, P1."

Figure 2:
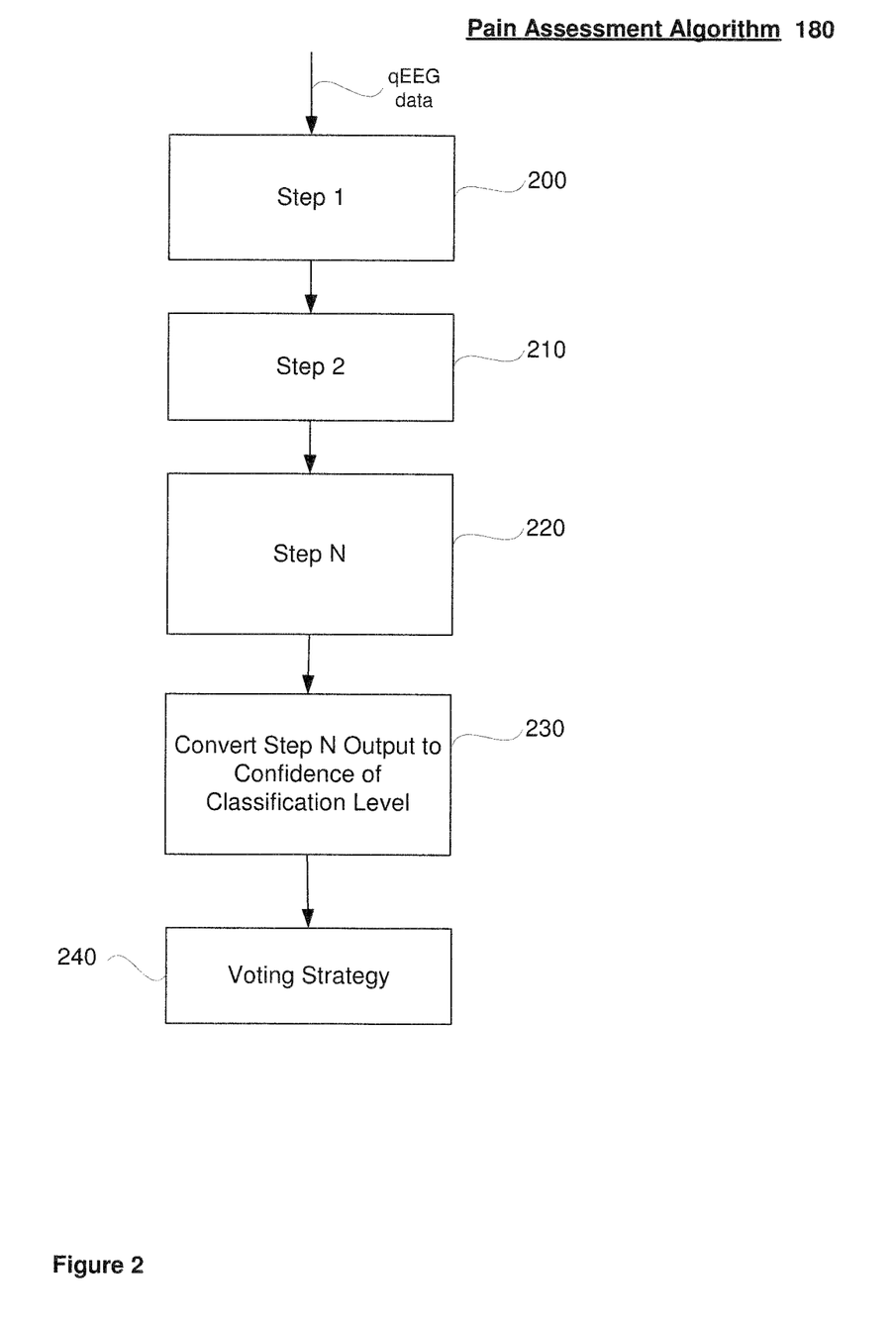
FIG. 2 shows a flow chart for an exemplary embodiment of a pain assessment algorithm according to the present invention.

The EEG data may be recorded in analog or digital format. If the data is recorded in analog format, this data is digitized and may then be subject to artifacting or any other quality assurance procedure as would be understood by those skilled in the art. After this, a selected set of features is extracted from the digital data of acceptable quality. In short, a selected set of features from the qEEG data which are particularly relevant to assessment of pain experienced are extracted from the overall data set obtained and compared to reference data including at least one of (i) population normative data indicative of brain wave activity of individuals in an absence of pain, (ii) population reference data indicative of brain wave activity of individuals generated in response to pain events inflicted thereon, (iii) subjective population reference data indicative of brain wave activity of individuals reporting a sensation of pain, and (iv) population of reference data indicative of brain wave activity of individuals following an intervention which has changed a subjective report of pain. Thereafter, in steps 130 and 135, respectively, univariate or multivariate (e.g., Mahalanobis distances) data features are computed for the extracted features and these features may be transformed (for example, log transformed) where appropriate to obtain a normal Gaussian distribution. As those skilled in the art would understand, the actual value of change or difference scores may alternately be used as criteria without these transforms or obtaining standard scores.

For example, in a first step of a procedure to extract the selected set of features, ANOVAS and other statistical methods are used to search out features "A" within the external qEEG database (or other criterion values) which are significantly different between two or more groups of interest (such as individual experiencing pain compared to individuals in an absence of pain). Then, results from the first step, the set of features "A" are input to a classifier function such as a multiple stepwise discriminant function, the results of which will be used (a) as a classifier function itself to later be considered as part of a pain assessment strategy and/or (b) to reduce the number of features to a more sensitive set of features "B" to be entered into the next step which may include, for example, cluster analysis. The set of features "B' is input to a cluster analysis the results of which will be used (a) as a classifier function itself for later consideration as part of the pain assessment strategy and/or (b) to reduce the number of features to a more sensitive set of features "C" which may be used alone or in combination with the feature sets "A" and/or "B" as inputs to logistic regression. Similarly, a neural network may be used which receives as input a large unselected set of features extracted from the qEEG data and which outputs a reduced set of features "D" which can be used as a classifier function itself to later be considered as part of the pain assessment strategy and/or to reduce the number of features to a more sensitive set of features combined with the set of features "A" and/or the set of features "B" and/or the set of features "C" to be entered in the logistic regression. Alternatively, as would be understood by those skilled in the art, a single classifier function may be used to estimate a probability that pain is being sensed and the results from this single classifier function may be compared to data from the database to make determinations regarding the presence/absence of pain and the intensity and/or type thereof.

Thereafter, as will be described in more detail below, the data is entered into the one or more classifier function(s) through which it is statistically associated with a subgroup representing individuals in similar or related states of pain within the database. Those skilled in the art will understand that, in place of the database, a look-up table or other structure representing similar data or other predefined criteria may be employed. By applying a decision making CLASSIFIER FUNCTION such as regression to the individual's data the statistical likelihood that the individual is properly classes within a group with a specified degree and/or type of pain will be determined. The Regression module, the preferred embodiment being Logistic Regression, fits a common slope cumulative model, which is a parallel lines regression model, based on the cumulative probabilities of the response categories rather than on their individual probabilities. Taking into account k predictive variables for n individuals, the model is:

$$\text{Log } [p_i/1-p_i] = \alpha + \beta_1 x_{i1} + \beta_2 x_{i2} + \ldots + \beta_k x_{ik}$$

This equation which has been previously trained on the database including individuals and subjects enduring varying amounts/types of pain is applied to the individual and a pain assessment is made. Those skilled in the art will understand that, in other embodiments any or a combination of discriminant functions, cluster algorithms, neural networks and/or other classifier functions will be applied to the data for the purpose of assessing pain.

Figure 3:
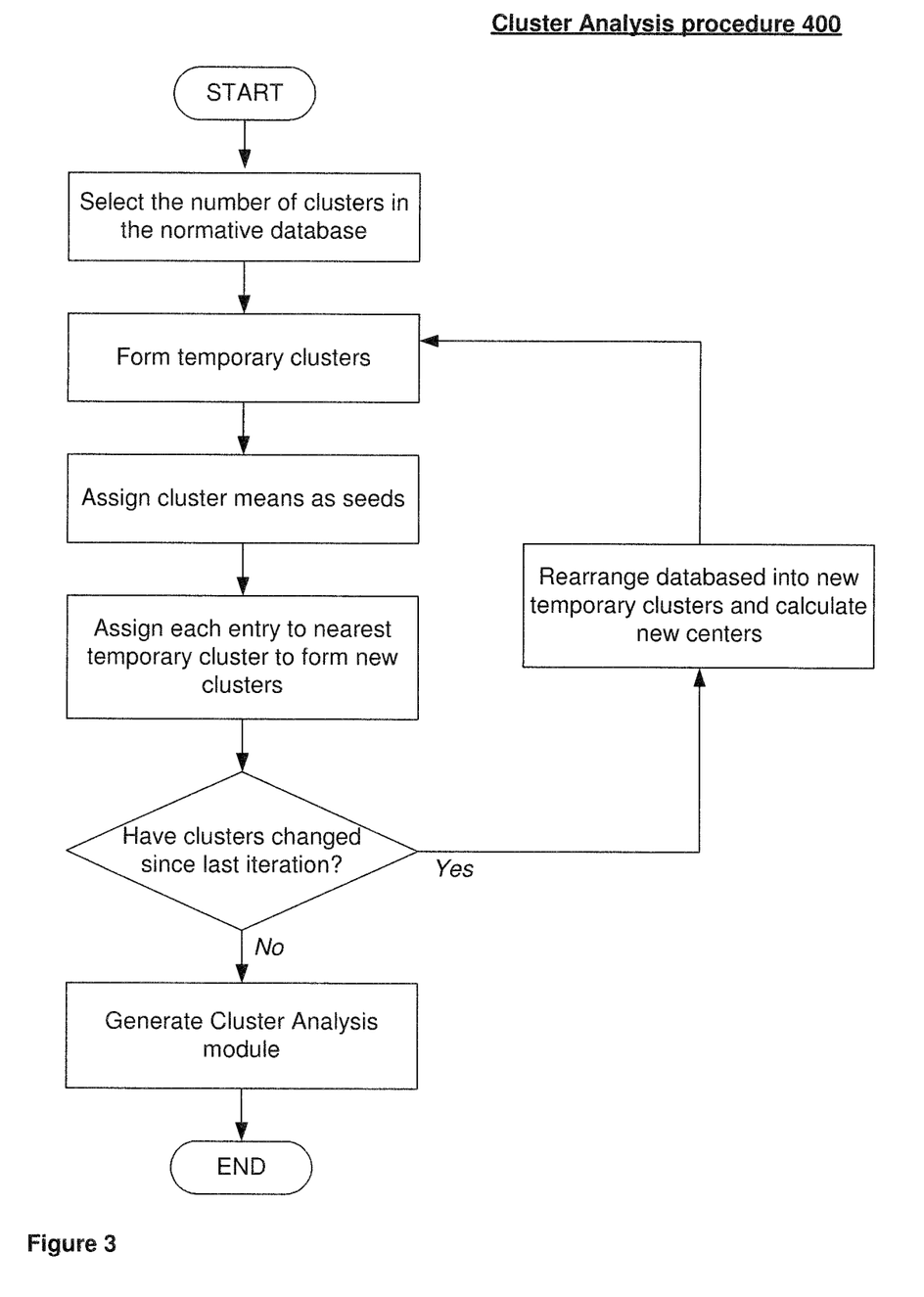
FIG. 3 shows a flow chart for an exemplary embodiment of a cluster analysis procedure used in developing a cluster analysis module utilized in the pain assessment algorithm.
Figure 4:
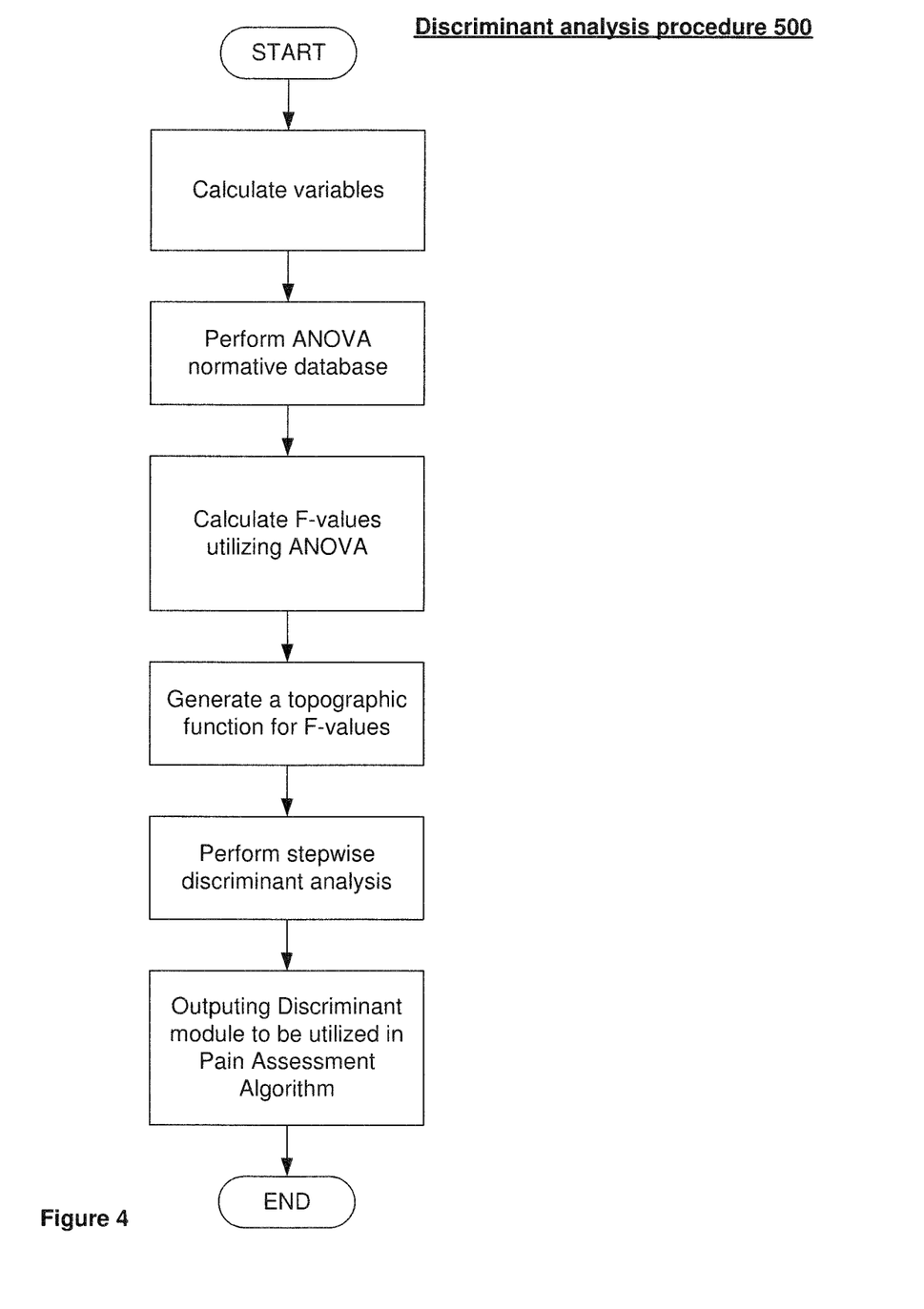
FIG. 4 shows a flow chart for an exemplary embodiment of a discriminant analysis procedure for developing a discriminant analysis module utilized in one embodiment of the pain assessment algorithm.

Those skilled in the art will understand that, although the exemplary embodiment of the pain assessment algorithm 180 described below specifically discloses steps for utilizing a Cluster Analysis module 400, a Discriminant Analysis module 500 and a Logistic Regression module, in that order, the pain assessment algorithm of the present invention may include some or all of these modules in any particular order. Furthermore, rules obtained by various other classifier modules, such as by using a neural network, may also be incorporated into the pain assessment algorithm 180 to generate a prediction of the expected cognitive decline of the patient. In addition, as those skilled in the art would understand, all of the modules utilized in the pain assessment algorithm 180 may be re-derived and/or modified following any or all changes to the database and improvements, refinements or future iterations of the classifier algorithms. However, in a preferred embodiment logistic regression is the final step in the procedure. For example, as shown in FIG. 2, in Step 1 (200) the selected features are input to a classification procedure such as, for example, a discriminant function to determine the relative probability of two or more levels of pain. The set of features identified in this analysis may also be input to other classifier functions such as cluster analysis and/or logistic regression.

For example, in Step 2 (210) the selected features are input to a classification procedure such as for example a cluster analysis to determine the relative probability that a subject is experiencing pain corresponding to that of two or more clusters reflecting different levels and/or types of pain. The set of features identified in this analysis can be used as selected input to other classifier functions such as discriminant analysis and or logistic regression.

Then, in step N (220), selected features are input to, for example, a classification procedure such as a regression and/or logistic regression to determine the relative probability of two or more states of pain. The set of features identified in this analysis may also be used as selected input to other classifier functions such as cluster analysis and/or discriminant function.

Thereafter, in step 230, the probability score computed by the classification function of Step N is converted to a confidence level using Receiver Operating Characteristic (ROC) Curves as would be understood by those skilled in the art. Using plots of sensitivity versus specificity, the probability corresponding to various P levels (such as 0.10, 0.05, 0.01, etc.) may be specified. Where the results of multiple classifier functions are used to make the pain assessment, they may be combined using a "voting strategy" in Step 240 as would be understood by those skilled in the art. In addition, the pain assessment algorithm may utilize additional data (e.g., data concerning pre-existing conditions, clinical history/symptoms, neurobiological Or genetic information) to further refine pain assessments.

In a similar manner, a "QSEP pain signature" will be derived from recordings from brain regions mediating painful sensations reflected as changes in the amplitude, peak latencies or intervals between peaks, area under the SEP between selected latency points, selected morphology descriptors or a neuroanatomical distribution of the patient's SEPs elicited by calibrated stimulation with different, calibrated intensities of constant current electrical or infrared laser pulses. These stimuli are delivered to particular places on the body surface (e.g., the median nerve on the wrist) or may be delivered directly to the dermatome or body surface region nearest to that reported as most severely painful. In such implementation, the SEP waveshapes may be compared quantitatively to a calibrated normative database or, if the pain is lateralized or otherwise localized, by comparison to SEPs elicited by stimulation of the afflicted versus the homologous or homotopic non-afflicted counterpart or control region. Quantitative SEP analyses (qSEP) may be performed using a variety of mathematical techniques, such as independent component analysis (ICA), principal component analysis (PCA) or t-tests between regions or between stimulation conditions or intensities to decompose the SEP into quantitative descriptors and compare the subject SEP descriptor values to normative descriptor values obtained from a normative or pain reference database analogous to those described above for the qEEG. The elements of the pain signature are used as variables in a "qSEP pain discriminant function. P2."

The qEEG and/or the qSEP are used to detect pain-related activity in the subject's brain waves as indicated by one or more parameters. In the qEEG, the parameters may include, but are not limited to, power in a particular wide band frequency domain (e.g., delta, theta, alpha, beta, gamma), or in some particular frequency quantified using very narrow band (VNB) spectral analysis in a preselected portion of the brain, coherence and/or asymmetry of power in any wide or VNB frequency band between the preselected portions of the brain, etc. In the qSEP, the parameters may include the latency periods, amplitude and/or area under any peak in preselected portions of the brain, coherence and/or asymmetry of total SEPs and/or individual peaks from any pair of homologous portions of the brain (inter-hemispheric), power ratio or asynchronization between any pair of electrodes on the same hemisphere (intra-hemispheric). In analysis of the qEEG and/or the qSEP, three-dimensional images of the current sources within the brain may be generated, and the parameters may include power and/or current flow and/or Z-score at any frequency in selected voxels in the brain or voltages which are related to particular peak latencies or latency intervals in the analysis epoch of the SEP waveshape.

As shown in FIG. 1, the PDI 16 is coupled to one or more EEG electrodes 8 which are applied to the scalp of a subject 20 being analyzed for the presence of pain in any chosen configuration (e.g., 10/20 system). When constructing the database 6, the electrodes 8 are coupled to the scalps of the individuals in the population. Those of skill in the art will understand that any conventional EEG biosensor electrodes may be used in conjunction with the present invention and that the electrodes 8 may be reusable or disposable. For example, the electrodes 8 may be pre-gelled, self-adhesive disposable electrodes. Alternatively, the electrodes 8 may have multiple small barbs, a needle electrode or a conductive disc temporarily attached to the scalp. The electrodes 8 may also utilize conductive gel to provide rapid and secure attachment to the scalp while limiting noise in the electrical signals returned by the electrodes 8. In other exemplary embodiments (e.g., a portable system), the electrodes 8 may be coupled to a cap placed on the head of the subject 20 and oriented to place the electrodes 8 in any chosen configuration relative to the scalp. The cap may facilitate placement of the electrodes 8 in a non-clinical setting and reduce problems associated with attachment of the electrodes 8 to the scalp. In another exemplary embodiment, the electrodes 8 may be contained in a self-adhering strip of material in an array. Thus, the PDI 16 may be configured to receive data from any number and/or type of biosensor electrodes and may be configured to separate data from groups of electrodes 8 allowing, for example, simultaneous use with multiple patients, e.g., in hospital beds, a neurotraumatology ICU, multi-hospital trauma network, etc. In this embodiment, the database 6 may be populated by several entities simultaneously. The electrodes 8 may be coupled to the PDI 16 via a wired or wireless connection. Using wired electrodes, leads may transfer signals from the electrodes 8 to the PDI 16, whereas, with wireless electrodes, radio frequency signals may transfer the signals to the PDI 16 using radio frequency transmitters. The PDI 16 includes a receiving arrangement (e.g., cable connector, radio frequency receiver) to receive signals from the electrodes 8. Because the PDI 16 may be configured to receive signals from electrodes on multiple subjects, the system 1 may be implemented over multiple hospital beds, a neurotraumatology ICU, a multi-hospital trauma network, etc.

A stimulator 13 may be coupled to (via a connector) or integral with the PDI 16 when, for example, monitoring the SEP and/or constructing the database 6. The stimulator 13 may inflict one or more pain events on the subject 20 and/or individuals in the population at some selected repetition rate, usually in the range of 5-11 pulses/second, or at random intervals. The stimulator 13 may include or be controlled by software for varying a type, intensity and/or duration of pain events to generate the SEP and brain activity simulating various types of pain, e.g., neuropathic, musculoskeletal or visceral, unilateral or bilateral, localized or generalized, acute or chronic, emotional or psychic pain, etc.

To compare regional sensitivities and to avoid habituation, stimulation sites and/or intensity may be controlled by the PDI 16. The pain events may vary in type and/or duration from simulating instantaneous pain to chronic pain. The stimulator 13 may use electrical, mechanical, chemical, optical and/or thermal mechanisms and/or auditory sounds or visual scenes to simulate the pain events. For example, the stimulator 13 may apply electrical shocks, laser stimulation, compressive force and/or temperature variations to the individual to elicit "physical pain." In one exemplary embodiment, the stimulator 13 applies a variable electric current or laser energy to a sensory nerve (e.g., the median nerve at the wrist, the posterior tibialis nerve at the ankle, the skin surface, etc.) so that an amount of pain inflicted may be accurately controlled while the PDI 16 measures brain activity of the individual(s) in conjunction with an onset of the pain event(s) to capture the SEP data, as well as other data corresponding to the pain experienced by the individual, e.g., qEEG, Auditory Evoked Potentials, Visual Evoked Potentials, EKG, etc.

Multimodal stimuli may be devised to distinguish between psychic pain (e.g., emotional or mental) and physical pain, and may include repeated presentations of graphic visual images or sounds, especially in evaluation of patients with post-traumatic stress disorder (PTSD).

The electrodes 8 may be placed over selected locations, or in the traditional 10/20 system, to harvest brain waves and generate the EEG and SEP data therefrom. These brain waves may also be utilized to construct a three-dimensional image of the brain using signal source localization algorithms, e.g., low resolution electromagnetic tomographic analysis (LORETA), variable resolution electromagnetic tomographic analysis (VARETA), etc. Using these methods regions of the brain may be evaluated and which may reflect awareness, quality and/or intensity of pain include, but are not limited to, the dorsolateral, mesial, midline and periorbital regions of the prefrontal cortex, the insula, the anterior, middle and posterior regions of the cingulate gyrus, the somatosensory regions of the central and parietal cortex, the amygdala, the putamen and the thalamus. The electrodes 8 may be placed over selected locations, or in the traditional 10/20 system to harvest brain waves and generate the EEG and SEP data therefrom.

The electrical signals monitored by the electrodes 8 are transferred to a high-gain, low-noise amplifier 17 in the PDI 16 and then filtered by a filtering arrangement 19 to detect and reject artifact contamination of the signals. Detection of the artifacts in the electrical signals may be accomplished by, for example, (1) detecting non-stationarities relative to statistical parameters derived from a sliding window of multiple successive 2.5 second long segments of the EEG, (2) applying a set of rules defining characteristics of common artifacts such as EMG (body), EKG (heart beats) and/or electro-oculogram (eye movements) and/or (3) using independent component analysis (ICA) to identify artifacts by multivariate statistical procedures, and/or fractal dimensional analysis. As understood by those of skill in the art, the filtering arrangement 19 minimizes the impact of noise and/or other artifacts resulting from, for example, subject movement, loosely applied electrodes, interference, etc. to generate data representative of and restricted to the brain activity of the subject 20. Electrodes may be protected by driven shields to reduce artifacts.

After artifact removal, the EEG may be subjected to spectral analysis using a signal processing technique such as, Fast Fourier Transform (FFT), wavelet analysis or fractal dimensional analysis performed on samples of the EEG approximately 2.5 seconds long. The EEG power spectrum may be divided into wide bands (e.g., low delta (0.5-1.5 Hz), high delta (1.5-3.5 Hz), theta (3.5-7.5 Hz), low alpha (7.15-10 Hz), high alpha (10.0-12.5 Hz), beta (12.5-25 Hz), low gamma (25-35 Hz), high gamma (35-50 Hz) and ultra high (50-200 Hz). The variance-covariance matrix of all frequencies in all leads versus all frequencies in all leads can be computed to evaluate the spectrum and the bispectrum. That is, phase relationships and coherence between and among different frequencies within and among all leads will be examined.

Alternatively, the spectrum may be divided into very narrow bands (VNB) of approximately 0.39-0.50 Hz in width. Absolute power and relative power, monopolar and bipolar derivations, bilateral symmetry, coherence and bicoherence between homologous leads, coherence and bicoherence and power gradients between all pairs of leads and multivariate compressions (e.g., Mahalanobis Distances) of various combinations of the above-listed features may be computed and expressed as scores (e.g., Z-scores) relative to normative distributions. Similarly, the fractal dimension can vary between one and two, a fractal database can be constructed, and fractal Z-scores may be computed for the EEG from different electrodes in the presence or absence of pain.

The amplifier 17 amplifies the electrical signals monitored by the electrode 8 using, for example, an amplification gain at approximately 100,000 dB, a high input impedance (~1 Megohm), a bandwidth of approximately 0.5 Hz-1500 kHz and/or a noise level of less than approximately 1 µV. The amplifier 17 may include an input isolation circuit to protect against current leakage, such as a photo-diode light-emitting diode isolation coupler, and may be protected from electrical interference by a radio-frequency filter and/or a 60-cycle notch filter as is known in the art. The amplified electrical signals from each electrode 8 are output by the amplifier 17 and converted to digital signals by an analog-to-digital converter (ADC) 18 which, in the exemplary embodiment, operates at a minimum conversion rate of approximately 8,000 samples per second and a resolution of 24 bits. Note that this may be accomplished by using a 24 bit digital amplifier for each electrode.

The digital signals are transmitted to a digital signal processor (DSP) 21 which may be included in or electrically coupled to a central processing unit (CPU) 25. The DSP 21 utilizes a digital signal processing technique to filter the digital signal as known in the art, and the CPU 25 compares the signals output by the DSP 21 to the reference data stored in the database 6, which may be stored locally in a memory in the PDI 16 (e.g., a nonvolatile memory) or remotely accessed via a network (e.g., the Internet, an intranet). Those of skill in the art will understand that the PDI 16 may be coupled to the network via a wired and/or wireless connection. As a result of the comparison, the CPU 25 outputs data indicating whether pain was detected and, if so, a magnitude of the pain (i.e., corresponding to the pain index). Analysis of the digital signal will be described further below.

The PDI 16 may include or be coupled to one or more input/output (I/O) arrangements 24. In the exemplary embodiment, the PDI 16 is coupled to a display for displaying brain wave data (i.e., EEG), the reference data and/or the pain index, etc. of the subject 20. The PDI 16 may include a keypad for configuring the components/settings of the PDI 16 and manipulating the EEG, a printer for printing the EEG and/or other subject-related data including the pain index and/or any other peripheral component integral with or coupleable to the PDI 16. To communicate with these and any other peripheral components, the PDI 16 preferably includes suitable hardware ports and software drivers for communicating with the components.

The qEEG analysis may reveal values of quantitative variables that exceed normative thresholds as identified in the database 6, indicative of the presence of pain. Alternatively, selected samples from the qEEG and/or SEP measurements may be input into one or more classifier functions, such as, for example, discriminant functions and/or regression equations to determine the existence/intensity of pain. A first discriminant function A estimates a probability that pain is being experienced (A=presence of pain) and a second discriminant function B estimates a probability that pain is not being experienced (B=absence of pain). Note that A may be the qEEG pain discriminant function, $\underline{P1}$, the qSEP pain discriminant function, $\underline{P2}$, or the sum, $\underline{P1+P2}$ multimodal qEEG plus qSEP pain discriminant function. Then, $e^A+e^B=1$, and $e^A/(1-e^B)$ equals a probability P that pain is present (from 0.00 to 1.00). A pain quantification index (PQI) may be calibrated to correspond to clinical scales of pain ranging from absent, sensation of discomfort, mild pain, moderate pain, severe pain and intolerable pain using this or any other suitable method. Those skilled in the art will understand that similar results may be obtained by training a neural network to arrive at the same conclusions. The system may be configured to determine that pain is being experienced by a subject whenever the value of the PQI is at least a threshold level t—i.e., whenever $e^A/(1-e^B)>t$. Depending on the consequences of false positives, this threshold level may be varied. For example, the system may determine the subject is sensing pain whenever the value of t is ≥0.95. For cases in which the consequences of a false positive are more severe the system may determine the subject is sensing pain whenever the value of t is ≥0.99. Furthermore, those skilled in the art will understand that actual data may give results of $e^A+e^B$ which, while approaching 1 may not equal 1.

When constructing the database 6, the CPU 25 instructs the stimulator 13 to administer pain events to the individual. For example, when performing an SEP assessment of sensitivity to pain in an individual, the CPU 25 instructs the stimulator 13 to administer trains of constant current electrical pulses at some repetition rate (e.g., approximately 9.7 Hz) to a pair of electrodes located over the median nerve at the wrist. Approximately 250 pulses, each having a square wave duration of approximately 200 µs, are administered in steps at intensities of about 5 mA to about 25 mA (or to a maximum intensity considered so painful by the individual as to be barely tolerable). The EEG data generated during administration of the pulses is subjected to spectral analysis (e.g., Fast Fourier Transform) at each intensity during an interval from pulse-to-pulse to detect an amplitude and phase of each very narrow band (VNB) frequency at intervals (e.g., approximately 0.5 Hz) across the bandwidth of the amplifier 17. Alternatively, successive samples of the EEG may be averaged with each sample beginning at an onset of each stimulus to a sample point just prior to an onset of a next stimulus in each pulse train (e.g., SEP latency epoch). Accordingly, a time series of voltages which are time-locked to pulse delivery times is constructed to represent the waveshape of the single somatosensory evoked potential elicited by each stimulus. Therefore, the brain activity data may either be used to construct the power spectrum or averaged to provide an updateable average SEP (ASEP) which is a sum of N samples (e.g., 250 SEP latency epochs time-locked to the onset of the stimuli divided by the number of samples) collected separately at each intensity. When computed, the power spectra and/or ASEP values may be stored in, for example, the memory of the PDI 16, a removable storage medium and/or transmitted to a remote storage device.

As understood by those skilled in the art, the brain electrical activity recordings data may be contaminated by voltage associated with body movements (e.g., eye movements), abnormal physiological events or ambient environmental electrical noise, etc. These voltages are typically greater than those created by brain activity, and the present invention utilizes algorithms to minimize any impact of such contaminating events. For example, as brain activity is detected through the EEG amplifiers, an updateable voltage threshold may be computed continuously for the EEG channel (or separately for each channel in the case of more than one EEG channel) by calculating a root mean square (rms)-voltage for a sliding 20-second window and multiplying the rms-voltage by a constant selected so that the rms-voltage is approximately 0.2 standard deviations of the amplitude of the electrical signals. The EEG is filtered to discard segments of the electrical signals containing voltages larger than the threshold. In the exemplary embodiment, the threshold is a multiple of the rms-voltage approximately equal to six (6) times the standard deviation of the amplitude. In other exemplary embodiments, the threshold may be a static value expected to be generated by brain activity (i.e., a value above which all voltages are considered to result from artifacts). After non-brain derived electrical activity has been removed from the recordings by these or similar denoising methods, the residual electrical signals may be assumed to be substantially artifact-free and are compiled to form a continuous, artifact-free sample of brain electrical activity to be used for further qEEG or qSEP processing. Ongoing brain electrical activity related to the EEG, as well as remaining non-brain derived electrical noise may be removed by denoising the SEP by the filtering arrangement 19 as described in U.S. Pat. No. 6,566,861, entitled "Fetal Brain Monitor," the entire disclosure of which is hereby expressly incorporated by reference.

It is important that means be provided enabling the PDI to adaptively monitor the quality of the data being acquired to ensure acceptable test-retest reliability and to ensure that adequate information is acquired while avoiding excessive and/or redundant data. This is particularly important since the data collection process may involve patient or subject discomfort. Although it may be desirable to maintain an option allowing the operator to collect a predetermined amount of data, there are numerous methods by which adaptive quality control may be more efficiently be accomplished. One exemplary means for achieving such self-evaluation of reliability is to compute a "coefficient of variation [Standard Deviation divided by Mean Value], or CV, for all variables of interest such as for example the VNB spectral power at each frequency or the SEP amplitude in each lead, progressively as data are acquired. Data are considered acceptably reliable, i.e., "replicable" when the CV converges to a preselected threshold defining acceptability. Alternatively, odd and even split halves may be constructed by assigning intervals alternately to two interlocked, but independent samples, each containing, for example, 10 light averages which are derived from approximately 25 stimuli to comprise a total of 250 "odd" and 250 "even" samples. The standard deviation within each of the split halves may be computed at each sample point of each light average as:

$$\sigma^2 = \left[\sum_{i=1}^{10} V^2/N\right] - \left[\sum_{i=1}^{10} (V/N)^2\right]$$

where $V$ = voltage at each time point $V^2/N$ = mean square of the voltage; and $(V/N)^2$ = squared mean of the voltage.

When the PDI 16 reveals that the individual is experiencing pain, the measures revealing it should preferably be reliably replicable. Replicability may be tested using the t-test at each time point t as follows:

$$t = \frac{(V_1 - V_2)}{|\sigma_{V_1}^2 + \sigma_{V_2}^2|^{1/2}}$$

In an alternative embodiment, a cross-correlation may be utilized across an entire wave with a threshold for minimum correlation which would be acceptable to indicate replicability. Once normative data is available for the means and the voltages at each time point, the present method may be used to detect and quantify the pain experienced by the subject 20. If pain is detected with a significance of P>0.05, for example, replication yields $p^2<0.0025$. Results from the two split-halves may be combined (i.e., averaged) for display, with replicated significant results highlighted.

In another exemplary embodiment, a digital comb filter is used to reduce the adverse effects of noise in the electrical signals. For example, the system 1 may employ a digital comb filter as described in U.S. Pat. No. 4,705,049 entitled "Interoperative Monitoring or EP Evaluation System Utilizing an Automatic Adaptive Self-optimizing Digital Comb Filter," the entire disclosure of which is expressly incorporated herein by reference. As noted above, the PDI 16 may utilize a digital comb filter to improve a signal-to-noise ratio (SNR) of the electrical signals gathered by the electrode(s) 8. In the digital comb filter, band pass frequencies are selected to form teeth of the comb using a phase variance parameter timed to correspond to the presence and absence of the pain events. As understood by those of skill in the art, optimal digital filtering may be an alternative to signal averaging for improving the SNR. For example, where the stimulator 13 produces approximately 250 somatosensory events with about 9.7 events per second for signal averaging, the SEP is synced to the pain events while the noise is random. When the SEP is calculated, the noise is reduced proportional to the square root of the number of stimuli, e.g., pain events. However, the signal averaging is relatively slow compared to the digital comb filtering. Since EEG and ambient noise can be approximately 100-250 µV, the residual non-SEP "noise" after simple signal averaging may remain as high as 15 µV. The peak to peak SEP amplitude is on the order of 2.5 µV. Thus, the signal to noise ratio may be as poor as 1:6. Further denoising is possible by using optimal digital filtering.

The ASEP data and/or the qEEG data is evaluated using a quantitative assessment of an expected normality (e.g., absence of pain) of the signals such as "Neurometrics" (the computerized quantitative analysis of brain electrical activity). In Neurometric analysis, features are extracted from the qEEG and the SEPs, transformed to obtain Gaussianity, compared to expected normative values (population/self norms as described above) and expressed in standard deviation units from the normal population (i.e., pain index). The results can be displayed as color-coded topographic probability maps of brain function, or color-coded segments of a curve in the time domain (voltage vs. latency). Utilizing these methods greatly enhances the sensitivity, specificity and clinical utility of such data. Profiles of the qEEG and SEP may be mathematically described in the presence of pain and compared to normative profiles in the absence of pain.

In order to evaluate the filtered SEP, an algorithm is applied to the SEP which automatically detects each of several peaks in a curve time-locked to the stimuli to identify the latency of each peak. For example, after 3-point smoothing of the filtered average, a resulting SEP is amenable to automatic peak detection by a procedure which hunts for zero-values of the second derivative and which outputs a series of time points corresponding to the peaks. The computed peaks are marked on the optimally filtered qSEP and superimposed on a normal template and, as described above, the latencies are compared to normative data collected from pain experiments on the control population and/or the subject 20 when not experiencing pain.

Figure 5:
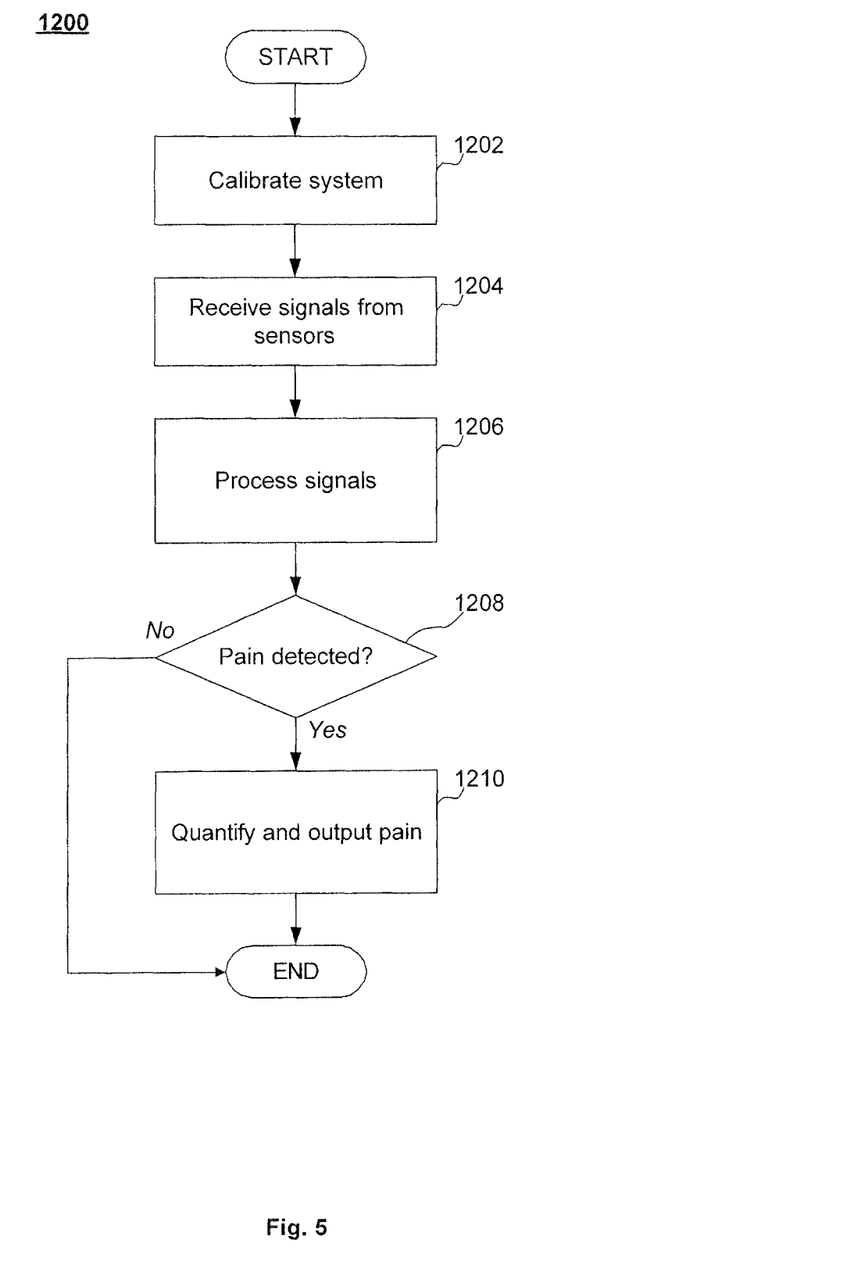
FIG. 5 shows an exemplary embodiment of a method for detecting pain according to the present invention.

An exemplary embodiment of a method 1200 for detecting pain in the subject 20 according to the present invention is shown in FIG. 5. In step 1202, the system 1 is initialized and calibrated. The PDI 16 and the I/O arrangement(s) 24 may be powered and configured for pain detection in accordance with the methodology described herein. The system 1 may be configured based on subject data, e.g., height, weight, age, medical history, etc. The subject data may be utilized when determining the existence and level of pain. For example, the database 6 may be queried based on the subject data and the subject's brain wave data.

In step 1204, the PDI 16 receives signals corresponding to the brain activity of the subject 20 (e.g., electrical signals from electrodes 8 attached to the scalp of the subject 20). In step 1206, the signals are processed by the PDI 16 in the manner described above. That is, the qEEG and/or the qSEP data of the subject 20 are used to generate data corresponding to the brain activity which corresponds to pain experienced by the subject 20. As described above, the signals are filtered and smoothed to reduce the effects of ambient noise and artifacts.

In step 1208, the brain activity data is compared to the reference data to determine whether pain exists. The brain wave data is compared to the reference data in the database 6, and a value corresponding to the pain index (i.e., corresponding to a level of pain experienced by the subject 20) is returned and output by the I/O arrangement 24. When the brain wave data is indicative of the presence of pain, the method may proceed to optional step 1210 where the pain is quantified a PQI.

The present invention allows objective corroboration of pain in a subject. The determination of the presence of pain is advantageous in clinical and non-clinical settings. For example, in a lawsuit, damages are often awarded based on pain suffered and whether or not the pain is treatable or chronic. Objective corroboration of pain allows the damages to be calculate more accurately.

It will be apparent to those skilled in the art that various modifications and variations can be made in the structure and the methodology of the present invention, without departing from the spirit or scope of the invention. Thus, it is intended that the present invention cover the modifications and variations of this invention provided they come within the scope of the appended claims and their equivalents.

What is claimed is:

1. A method for detecting pain in a subject, comprising the steps of:
    inputting, using a processor, quantitative electroencephalogram (qEEG) data generated based on brain wave activity of the subject into a first classifier function A indicating a first probability score that pain is being sensed;
    inputting, using the processor, the qEEG data into a second classifier function B indicating a second probability score that pain is not being sensed;
    generating, using the processor, a probability P that the subject is experiencing pain as a function of the first and second probability scores;
    comparing, using the processor, the probability P to a threshold level to determine a presence of pain when the probability P is at or above the threshold level, wherein the pain is not elicited by a sensory stimulus,
    wherein the first classifier function A and the second classifier function B are independently generated from reference data comprising at least one of
        (i) population normative qEEG data indicative of brain wave activity of a first plurality of individuals in an absence of pain,
        (ii) population reference qEEG data indicative of brain wave activity of a second plurality of individuals generated in response to pain events inflicted on the second plurality of individuals,
        (iii) self normative qEEG data indicative of brain wave activity of the subject in an absence of pain, and
        (iv) subjective population reference qEEG data indicative of brain wave activity of a third plurality of individuals reporting a sensation of pain; and
    generating, using the processor, a pain quantification index (PQI) value based on a comparison of the qEEG data to the reference data, the PQI corresponding to an intensity of pain experienced by the subject when the presence of pain is detected.

2. The method according to claim 1, wherein the PQI includes values corresponding to one of a plurality of levels of pain and a plurality of types of pain, the types of pain include chronic and acute.

3. The method according to claim 1, further comprising: regulating an amount of analgesic administered to the subject by an apparatus as a function of the PQI.

4. The method according to claim 1, further comprising: directing, using the processor, a display to display the PQI, wherein the PQI corresponds to a clinical scale of pain comprising absent, sensation of discomfort, mild pain, moderate pain, severe pain and intolerable pain.

5. A device for detecting a pain in a subject, comprising:
    a receiving arrangement configured to receive electrical signals from a plurality of electroencephalogram (EEG) electrodes;
    a processor configured to generate quantitative EEG (qEEG) data based on brain wave activity of the subject detected by the EEG electrodes; and
    a memory storing reference data comprising at least one of
        (i) population normative qEEG data indicative of brain wave activity of a first plurality of individuals in an absence of pain,
        (ii) population reference qEEG data indicative of brain wave activity of a second plurality of individuals generated in response to pain events inflicted on the individuals,
        (iii) self normative qEEG data indicative of brain wave activity of the subject in an absence of pain, and
        (iv) subjective population reference qEEG data indicative of brain wave activity of a third plurality of individuals reporting a sensation of pain; and
    wherein the processor is coupled to the receiving arrangement and the memory, and configured to input the qEEG data into a first classifier function A indicating a first probability score that pain is being sensed and a second classifier function B indicating a second probability score that pain is not being sensed, the first classifier function A and the second classifier function B being independently generated by the processor from the reference data, to generate a probability P that the subject is experiencing pain as a function of the first and second probability scores, and to compare the probability P to a threshold level to determine a presence of pain when the probability P is at or above the threshold level,
    wherein the pain is not elicited by a sensory stimulus, and wherein the probability P equals:

$$\frac{e^A}{(1-e^B)}.$$

6. The device according to claim 5, wherein the receiving arrangement is one of a cable connector and a wireless signal receiver.

7. The device according to claim 5, wherein the receiving arrangement comprises at least one of an amplifier, an analog-to-digital converter, and a filtering arrangement.

8. A method for detecting pain in a subject, comprising the steps of:
inputting, using a processor, quantitative electroencephalogram (qEEG) data generated based on brain wave activity of the subject into a first classifier function A indicating a first probability score that pain is being sensed;
inputting, using the processor, the qEEG data into a second classifier function B indicating a second probability score that pain is not being sensed;
generating, using the processor, a probability P that the subject is experiencing pain as a function of the first and second probability scores;
comparing, using the processor, the probability P to a threshold level to determine a presence of pain when the probability P is at or above the threshold level, wherein the pain is not elicited by a sensory stimulus, wherein the first classifier function A and the second classifier function B are independently generated from reference data comprising at least one of
(i) population normative qEEG data indicative of brain wave activity of a first plurality of individuals in an absence of pain,
(ii) population reference qEEG data indicative of brain wave activity of a second plurality of individuals generated in response to pain events inflicted on the second plurality of individuals,
(iii) self normative qEEG data indicative of brain wave activity of the subject in an absence of pain, and
(iv) subjective population reference qEEG data indicative of brain wave activity of a third plurality of individuals reporting a sensation of pain; and
determining, using the processor, one of a predicted intensity and a predicted type of pain by comparing the qEEG data to the reference data using a logistic regression, when the presence of pain is detected.

9. The method according to claim 8, wherein the first and second classifier functions, A and B, respectively, are discriminant functions.

10. The method according to claim 8, wherein the threshold level is at least 0.95.

11. The method according to claim 8, wherein the threshold level is at least 0.99.

12. The method according to claim 8, wherein at least one of the first classifier function A and the second classifier function B is generated by the processor using a neural network.

13. The method according to claim 8, wherein the reference data further comprises at least one of medical histories, physical examination results and neurological examination results.

14. The method according to claim 8, wherein the qEEG data is generated from the brain wave activity of the subject detected by a plurality of EEG electrodes removably connected to at least one of a scalp and a forehead of the subject.

15. The method according to claim 14, wherein the plurality of EEG electrodes detect a series of voltage oscillations corresponding to the brain wave activity of the subject.

16. The method according to claim 8, wherein the subject is human.

17. The method according to claim 8, wherein the subject is one of a cat, dog, horse and nonhuman primate.

18. The method according to claim 8, further comprising:
generating, using the processor, an output signal directing an adjustment to delivery of an analgesic or an adjustment to treatment via a neurofeedback paradigm, when the presence of pain is detected.

19. A method for detecting pain in a subject, comprising the steps of:
inputting, using a processor, quantitative electroencephalogram (qEEG) data generated based on brain wave activity of the subject into a first classifier function A indicating a first probability score that pain is being sensed;
inputting, using the processor, the qEEG data into a second classifier function B indicating a second probability score that pain is not being sensed; and
generating, using the processor, a probability P that the subject is experiencing pain as a function of the first and second probability scores,
comparing, using the processor, the probability P to a threshold level to determine a presence of pain when the probability P is at or above the threshold level, wherein the pain is not elicited by a sensory stimulus,
wherein the first classifier function A and the second classifier function B are independently generated from reference data comprising at least one of
(i) population normative qEEG data indicative of brain wave activity of a first plurality of individuals in an absence of pain,
(ii) population reference qEEG data indicative of brain wave activity of a second plurality of individuals generated in response to pain events inflicted on the second plurality of individuals,
(iii) self normative qEEG data indicative of brain wave activity of the subject in an absence of pain, and
(iv) subjective population reference qEEG data indicative of brain wave activity of a third plurality of individuals reporting a sensation of pain, and
wherein the probability P equals:

$$\frac{e^A}{(1-e^B)}.$$

20. A device for detecting a pain in a subject, comprising:
a receiving arrangement configured to receive electrical signals from a plurality of electroencephalogram (EEG) electrodes;
a processor configured to generate quantitative EEG (qEEG) data based on brain wave activity of the subject detected by the EEG electrodes;
a memory storing reference data comprising at least one of
(i) population normative qEEG data indicative of brain wave activity of a first plurality of individuals in an absence of pain,
(ii) population reference qEEG data indicative of brain wave activity of a second plurality of individuals generated in response to pain events inflicted on the individuals,
(iii) self normative qEEG data indicative of brain wave activity of the subject in an absence of pain, and
(iv) subjective population reference qEEG data indicative of brain wave activity of a third plurality of individuals reporting a sensation of pain, wherein the processor is coupled to the receiving arrangement and the memory, and configured to input the qEEG data into a first classifier function A indicating a first probability score that pain is being sensed and a second classifier function B indicating a second probability score that pain is not being sensed, the first classifier function A and the second classifier function B being independently generated by the processor from the reference data, to generate a probability P that the subject is experiencing pain as a function of the first and second probability scores, and to compare the probability P to a threshold level to determine a presence of pain when the probability P is at or above the threshold level, wherein the pain is not elicited by a sensory stimulus; and
a display,
wherein the processor is further configured to generate a pain quantification index (PQI) value based on a comparison of the qEEG data to the reference data, the PQI corresponding to an intensity of pain experienced by the subject when the presence of pain is detected, and
wherein the display is configured to display the PQI, the PQI corresponding to a clinical scale of pain comprising absent, sensation of discomfort, mild pain, moderate pain, severe pain and intolerable pain.

21. The device according to claim 20, wherein the PQI includes values corresponding to one of a plurality of levels of pain and a plurality oft, pes of pain, the types of pain include chronic and acute.

* * * * *

UNITED STATES PATENT AND TRADEMARK OFFICE
CERTIFICATE OF CORRECTION

PATENT NO. : 10,898,130 B2
APPLICATION NO. : 15/195716
DATED : January 26, 2021
INVENTOR(S) : John et al.

Page 1 of 1

It is certified that error appears in the above-identified patent and that said Letters Patent is hereby corrected as shown below:

In the Claims

Claim 21, Column 19, Line 28:
"of pain and a plurality oft, pes of pain, the types of pain" should read "of pain and a plurality of types of pain, the types of pain".

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*